United States Patent [19]

Castiglia

[11] 4,022,197
[45] May 10, 1977

[54] BODY SUPPORT AND PROTECTION APPLIANCE

[75] Inventor: Ignatius F. Castiglia, New York, N.Y.

[73] Assignee: Thermo-Mold Medical Products, Inc., Burlington, N.J.

[22] Filed: May 4, 1976

[21] Appl. No.: 683,081

[52] U.S. Cl. .................. 128/101; 128/78; 128/96; 128/169; 128/540; 128/541; 128/578
[51] Int. Cl.² .................. A61F 5/02; A61F 13/02
[58] Field of Search ........... 128/78, 169, 587, 90, 128/545, 541, 96–101, 540, 157, 578, 80 R; 2/36

[56] References Cited

UNITED STATES PATENTS

| | | | |
|---|---|---|---|
| 2,520,063 | 8/1950 | Rishcoff | 128/78 X |
| 3,307,535 | 3/1967 | Locke | 128/78 |
| 3,400,710 | 9/1938 | Goldstein | 128/78 |
| 3,561,436 | 2/1971 | Gaylord, Jr. | 128/87 R |
| 3,570,480 | 3/1971 | Stubbs | 128/78 |
| 3,578,773 | 5/1971 | Schultz | 128/78 |
| 3,598,114 | 8/1971 | Lewis | 128/78 |
| 3,888,245 | 6/1975 | Berntson | 128/78 |
| 3,906,943 | 9/1975 | Arluck | 128/90 |

Primary Examiner—Aldrich F. Medberry
Attorney, Agent, or Firm—Flynn & Frishauf

[57] ABSTRACT

An appliance for supporting and/or protecting body portions comprises a pair of substantially rigid sheet-like members adapted to engage against predetermined spaced portions of the body of a wearer. The sheet-like members are coupled together at one end by means of a relatively large expanse of elastic material and are detachably connected together at the other end also by means of elastic material, the resulting structure encircling a body portion. This construction permits substantial contraction and expansion of the encircled body portion without substantially restraining the encircled body portion from expansion.

15 Claims, 8 Drawing Figures

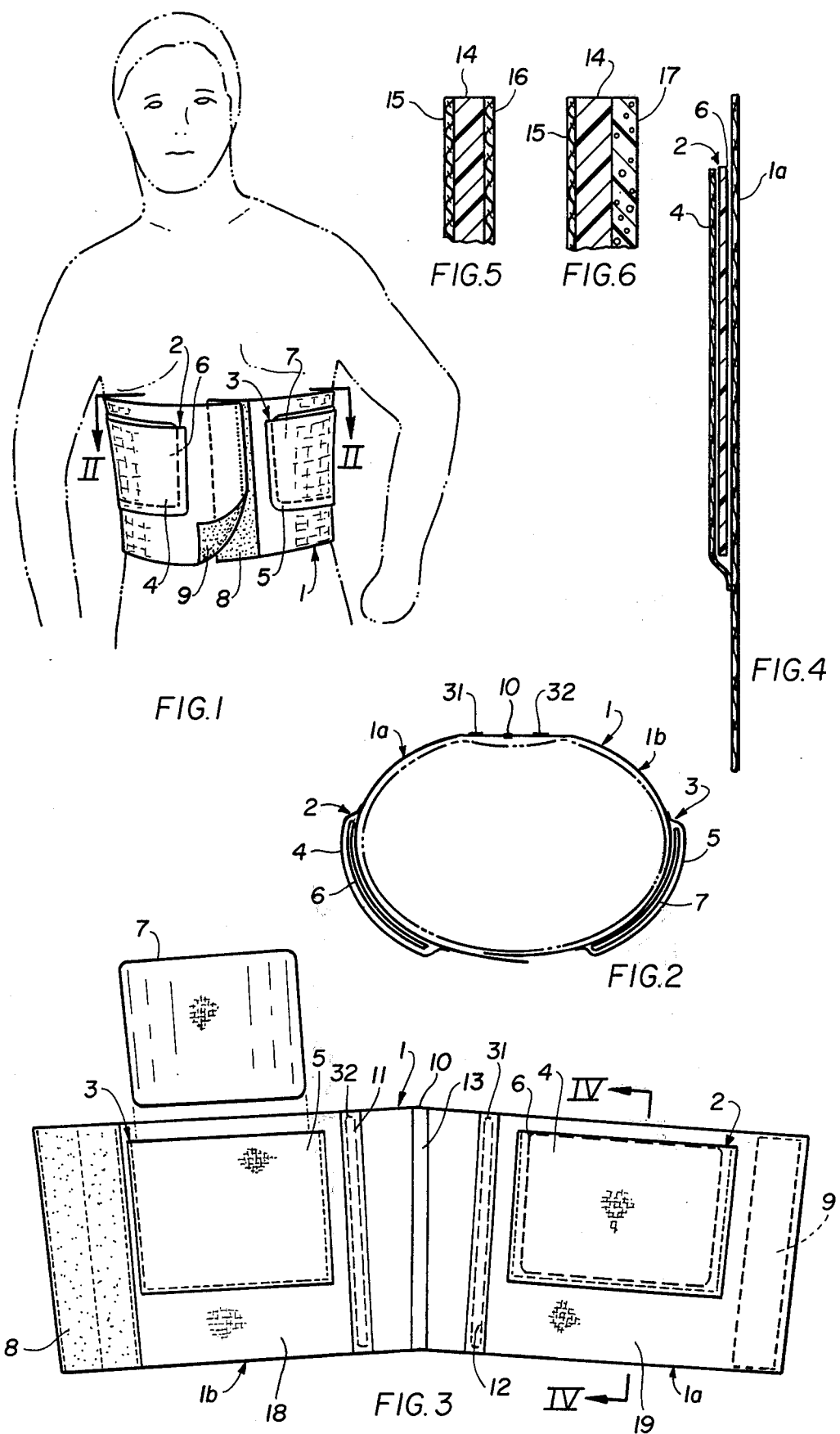

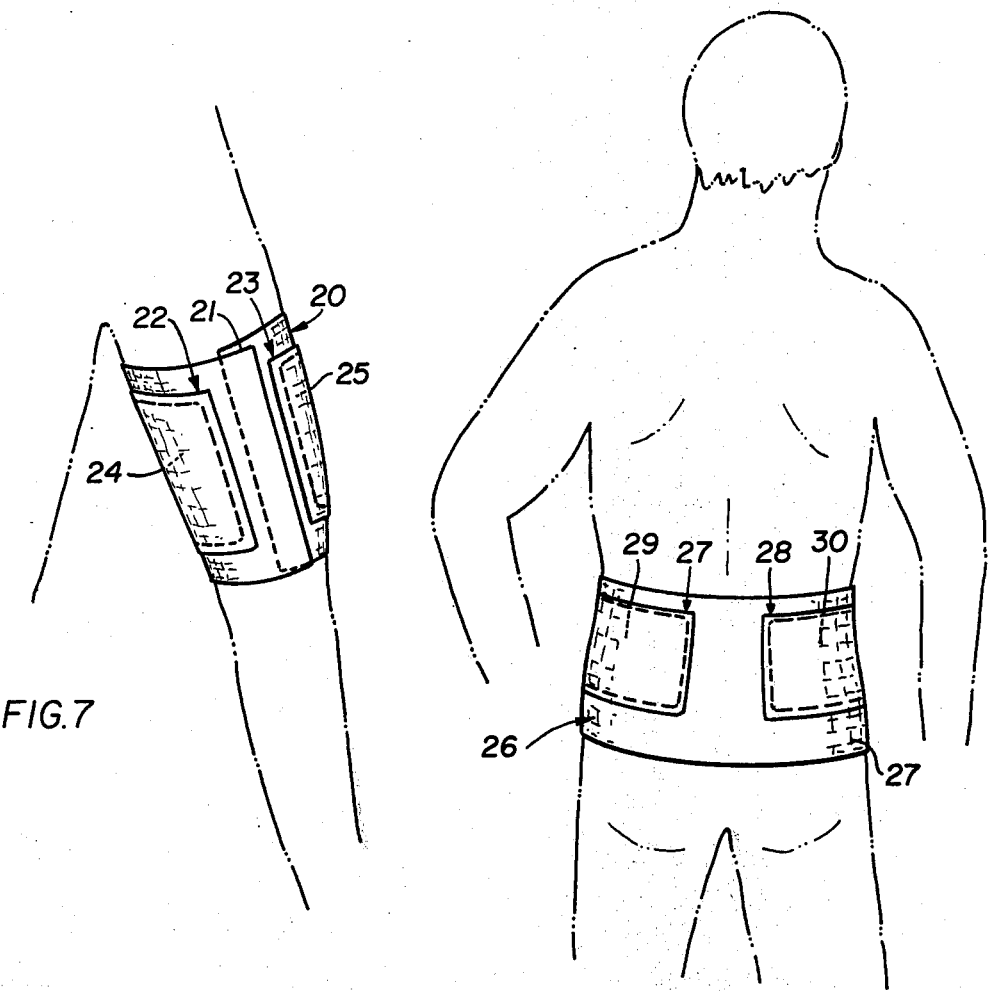

BODY SUPPORT AND PROTECTION APPLIANCE

This invention relates to appliances which support and/or protect portions of the body of a wearer, such as, for example, the rib cage.

Numerous support and protection appliances are known. However, such known appliances for protecting the rib cage or other body portions of a wearer do not provide the capability for easily achieving a precise fit to the wearer while also providing for substantially complete mobility and freedom of body movement and a high degree of protection and support to the wearer. These characteristics which are unobtainable in combination with the prior art devices are extremely important in many applications, such as in protection appliances for athletes for protecting damaged or vulnerable body areas under actual playing conditions.

The main object of the present invention is to provide an protection and support device for a body portion which has at least two substantially rigid sections which are easily deformable, for example under heat, to precisely conform to the body contours of a wearer, and wherein the deformable portions are interconnected by substantial elastic portions to retain the deformable, substantially rigid portions substantially in a fixed position relative to the body and to maintain the deformable portions substantially independent of each other in said substantially fixed position on the body regardless of expansion and contraction of the body portion in question.

A further object of the invention is to provide such an appliance which is particularly suitable for protecting the rib cage area of a wearer and which will also provide for substantially complete mobility and freedom of movement of the wearer while also providing a high degree of protection and support.

SUMMARY OF THE INVENTION

In accordance with the present invention, a body support and/or protection appliance comprises a first elastic section adapted to extend across a body portion of a wearer and a pair of substantially rigid sheet-like members coupled to end portions of the first elastic sections and being adapted to engage against predetermined portions of the body of a wearer. Second and third elastic sections are respectively provided at the ends of the substantially rigid members remote from the first elastic section for detachably and elastically connecting the remote ends of the substantially rigid members together with at least a portion of at least one of the second and third elastic sections interposed therebetween, to encircle a body portion of the wearer. The elastic sections permit substantial contraction and expansion of the encircled body portion of the wearer while simultaneously retaining the substantially rigid members adjacent the predetermined body portions of the wearer during the contraction and expansion, without substantially restraining the body from expansion.

The device may take the form of a substantially completely elastic belt-like member with pockets therein for receiving the sheet-like members such that they engage against the predetermined body portions of the wearer.

BRIEF DESCRIPTION OF THE DRAWINGS

FIG. 1 illustrates a typical body support and/or protection appliance according to the present invention in position on the body of a wearer to protect the rib cage of the wearer;

FIG. 2 is a top view of the device shown in FIG. 1 taken in the direction of the arrows II—II;

FIG. 3 illustrates the appliance of FIG. 1 in the opened state with one of the protective inserts removed from its associated pocket;

FIG. 4 shows a cross-section of the appliance of FIG. 3 taken along the line IV—IV;

FIG. 5 is an enlarged cross-sectional view of a typical protective insert for use in the present invention;

FIG. 6 is an enlarged sectional view of another protective insert for use in the present invention;

FIG. 7 illustrates another embodiment of the present invention for use in protecting the thigh or other leg portions of a wearer; and FIG. 8 illustrates an appliance according to the present invention for use in protecting the kidney area, or the like, of a wearer.

DETAILED DESCRIPTION

Referring to FIGS. 1–4, a body support and/or protection appliance of the present invention which is particularly suitable for protecting and supporting the rib cage area of a wearer is shown. The appliance comprises an elastic belt member generally designated by the reference numeral 1 with pockets 2,3 formed therein, for example by stitching an elastic material 4,5 to the main portion of the elastic belt member 1. In the pockets 2,3 are inserted substantially rigid members of heat deformable material 6,7 which are located by the pockets 2,3 to be adjacent the rib cage area of the wearer when the belt is mounted to the body of the wearer. The front portion of the belt 1 has fasteners, such as Velcro fasteners 8,9 for closing the belt on the wearer. Other fasteners, such as hooks, or the like, can be used to provide secure but adjustable fastening of the belt. The rear portion of the belt, as shown in FIGS. 2 and 3, comprises substantially rigid, elongated stays 31,32 for preventing buckling of the elastic portion of the belt when installed on the wearer. The stays 31,32 may be secured directly to the belt 1 by means of stitching 11,12 or by means of adhesives, or may be located in pockets stitched to the main portion of the belt 1. The belt 1 comprises, in the embodiment shown, two sections 1a and 1b which are stitched together at the midportion 10, the portions 1a and 1b being connected together at an angle relative to each other so that the upper and lower edges thereof slope downwardly. This provides a better fit to the chest area of the wearer of the device. An overlay 13 of fabric or elastic is secured to belt 1 by, for example stitching, to cover the seam between belt portions 1a and 1b.

The substantially rigid inserts 6,7 are preferably of a plastic heat deformable material such as, for example, the plastic sheet material alone or covered as disclosed in U.S. Pat. No. 3,906,943, the entire contents of which are incorporated herein by reference. The inserts 6,7 are heat formed to conform to the body of the wearer as disclosed in said U.S. Pat. No. 3,906,943. Other suitable materials can also be used.

In FIG. 4 the insert 6 is shown as a unitary structure of plastic material. However, as discussed above, the inserts 6,7 are preferably of a plastic heat deformable material 14 with fabric layers 15,16 on opposite sides thereof as disclosed in said U.S. Pat. No. 3,960,943. One of the fabric layers 15,16 which are securely adhered to the central plastic layer 14, is preferably of an insulating material to prevent heat from the heated up insert from being uncomfortably transmitted to the body of the wearer when the insert is being formed to conform to the body contours of the wearer.

As shown in FIG. 6, the central plastic material 14 may be provided with a foam layer 17 to replace one of the fabric layers. In use, the foam layer 17 is directed toward the body of the wearer to provide additional cushioning to provide impact absorption characteristics to the device of the present invention, thereby not only making the device more comfortable in normal use, but also providing additional protection to the user. The foam layer 17 also acts as the insulating layer when conforming the insert to the body contours of the wearer. A foam covered plastic member is disclosed, for example, in U.S. Pat. No. 2,800,129.

An important characteristic of the appliance of the present invention is that substantially rigid protection and support members are provided adjacent the areas of the body which are to be protected or supported. These protective portions are interconnected together at both sides thereof by substantially large elastic areas. When used in the chest area, it is seen that a substantial portion in the front portion of the chest area between the rib cage is covered only with elastic, and that the rear portion of the appliance between the rigid portions 6,7 is a wide expanse of elastic material. This unique construction provides protection and support to vulnerable or damaged areas of the body, but also permits a high degree of expansion and contraction of the body substantially without undue restriction and while also maintaining the protection and support members 6,7 in the proper relative positions against the body portions which they are to protect. When the device of the present invention is used to protect the rib cage area of an athlete, for example a football player, the device must provide proper protection under all playing conditions, even when the player is breathing extremely heavily which causes a great degree of expansion and contraction of the chest area. The relatively wide expanses of elastic material at both the front central chest area and the rear back area allows the device to expand without substantially restricting expansion of the chest of the wearer, but also maintains the substantially rigid members 6,7 in the proper positions against the rib cage of the wearer. In prior art devices which have a substantially non-expandable member extending across the complete front of the wearer and around the rib cage, such unrestricted expansion of the chest of the player is not possible.

The device of the present invention also has a large skirt area below the retaining pockets 3,4, the lower skirt areas 18,19 being of elastic material and preferably being integral with the remaining portions of the belt. The skirt areas 18,19 prevent slipping of the device in use and further enhances the value of the device to active people, such as athletes, or the like.

The elastic material 4,5 forming the outer portions of the pockets is elastic material preferably of the same type as the remaining portion of the appliance. The feature whereby the complete appliance except for the rigid inserts 6,7, and the stays 31,32, is of elastic material further enhances the ability of the device of the present invention to allow for substantial contraction and expansion of the body portion being protected and/or supported without unduly restricting the movement of the wearer.

The device of the present invention may be used on other portions of the body. FIG. 7 shows the use of a device according to the present invention on the thigh portion of a wearer. The device 20 is of elastic material and has pockets 22,23 formed therein by overlying pieces of elastic material secured thereto, preferably by stitching. Substantially rigid members 24,25 are inserted in the pockets and are preferably molded to conform to the contour of the leg areas being protected. The elastic belt member 20 is secured together at 21 for example by means of Velcro material in a manner similar to that shown in FIG. 1. Other adjustable closure means could be used. Preferably, the substantially rigid members 24,25 are of the same preferred constructions as members 6,7 discussed hereinabove. The device of FIG. 7 could also be used on arms and other portions of the legs, as required.

FIG. 8 shows a device according to the present invention used to protect the lower side and back areas, for example the kidney area of the wearer. Such a device is particularly useful for protecting boxers, or the like. The device of FIG. 8 comprises an elastic belt member 26 with pockets 27,28 formed therein for removably receiving substantially rigid inserts 29,30. The inserts 29,30 are preferably molded to the body and are preferably of the same type as discussed above in connection with inserts 6,7. The elastic belt member 26 has a large skirt area 27 below the substantially rigid inserts to prevent the belt member from slipping relative to the body of the wearer. The large skirt member could alternatively be placed above the substantially rigid members 29,30, rather than below as shown in FIG. 8.

More than two substantially rigid inserts, with elastic sections therebetween, may be provided, depending upon the particular application.

While the belt portion 1,20,26 of the devices according to the present invention is shown herein as being completely of elastic material, an alternative structure is possible whereby the elastic portions 4,5 are of inelastic material and are secured to the underlying belt 1. Alternatively, the section of the belt 1 in the area of the pockets for receiving the substantially rigid members 6,7 could be of inelastic material interconnected by the remaining substantially large portions of the belt 1. This construction would be, however, less advantageous than the construction illustrated in the Figures. Additionally, while the substantially rigid members are shwon as being removably retained in the pockets, they may be permanently mounted therein. The precise shape of the device may also be altered, as suits the requirements. For example, in some applications, it may be necessary to provide relief at the upper portions of the belt to provide additional clearance at the armpits of the wearer. The above and other modifications may be made to the present inventive concept as set forth in the accompanying claims.

I claim:

1. A body support and/or protection appliance comprising:
 a first elastic section adapted to extend across a body portion of a wearer;
 a means for substantially independently engaging against predetermined spaced portions of the body of a wearer, comprising a pair of substantially rigid sheetlike members coupled to end portions of said first elastic section; and
 second and third elastic sections respectively at the ends of said substantially rigid members remote from said first elastic section for detachably and elastically connecting said remote ends of said substantially rigid members together with at least a portion of at least one of said second and third elastic sections interposed therebetween to encircle a body portion of a wearer such that said elastic sections resiliently separate said substantially rigid members to permit substantial contraction and expansion of the encircled body portion of the wearer while retaining said substantially rigid members adjacent said predetermined body portions of the wearer during said contraction and expansion, without substantially restraining the body from expansion.

2. An appliance according to claim 1 comprising a first pocket member interposed between said first and second elastic sections and a second pocket member interposed between said first and third elastic sections, said first and second pocket members receiving a respective one of said substantially rigid sheet-like members.

3. An appliance according to claim 2 wherein said pocket members each have an opening for removably receiving said respective substantially rigid sheet-like members therein.

4. An appliance according to claim 1 wherein said substantially rigid sheet-like members are heat deformable and are moldable, in the heated condition, to conform to the contours of a body portion of a wearer, and substantially retain their contour molded condition upon cooling.

5. An appliance according to claim 4 wherein said sheet-like members are plastic members with a fabric layer on at least one surface thereof.

6. An appliance according to claim 5 wherein said sheet-like members have fabric layers on both sides thereof.

7. An appliance according to claim 5 wherein said sheet-like members have a foam layer on one surface thereof, said foam layer being directed toward the body of a wearer.

8. An appliance according to claim 2 wherein said first and second pocket members are of elastic material.

9. An appliance according to claim 8 wherein said first pocket is integral with at least a portion of said first elastic section and is integral with said second elastic section, and wherein said second pocket is integral with at least a portion of said first elastic section and is integral with said third elastic section.

10. An appliance according to claim 1 wherein said second and third elastic sections have free ends with adjustable interengaging fastening members thereon for adjustably encircling a body portion of a wearer.

11. An appliance according to claim 1 wherein said first elastic section comprises a substantially rigid stay member extending substantially transversely thereof.

12. An appliance according to claim 8 further comprising a skirt portion of elastic material below said respective pockets for engagement against a body portion of a wearer to prevent slipping relative to the body portion of the wearer.

13. An appliance according to claim 1 wherein said sheet-like members are formed to conform to the respective rib cage areas of a wearer, and wherein said first elastic section is adapted to extend across a substantial portion of the back of the wearer and said second and third sections are adapted to extend across a portion of the chest area of the wearer so as to provide an elastic section in the chest area of the wearer between said sheet-like members.

14. An appliance according to claim 8 wherein said sheet-like members are formed to conform to the respective rib cage areas of a wearer, and wherein said first elastic section is adapted to extend across a substantial portion of the back of the wearer and said second and third sections are adapted to extend across a portion of the chest area of the wearer so as to provide an elastic section in the chest area of the wearer between said sheet-like members.

15. An appliance according to claim 2 further comprising at least two skirt portions of elastic material adjacent said respective pockets, one of said skirt portions extending between said first and second elastic sections and the other of said skirt portions extending between said first and third elastic sections, to prevent slipping relative to the body portion of the wearer.

* * * * *